US008986973B2

(12) United States Patent
Kang et al.

(10) Patent No.: US 8,986,973 B2

(45) Date of Patent: Mar. 24, 2015

(54) ***STREPTOCOCCUS DYSGALACTIAE* ID9103 AND METHOD FOR PRODUCTION OF HYALURONIC ACID USING THE SAME**

(71) Applicant: Ildong Pharm Co., Ltd., Seoul (KR)

(72) Inventors: Dae-Jung Kang, Yongin-si (KR); Jong-Hyuk Im, Gwacheon-si (KR); Tae-Yoon Kim, Hwasung-si (KR); Jae-Hoon Kang, Seoul (KR)

(73) Assignee: Ildong Pharm Co., Ltd., Seoul (KR)

( * ) Notice: Subject to any disclaimer, the term of this patent is extended or adjusted under 35 U.S.C. 154(b) by 0 days.

(21) Appl. No.: 14/226,216

(22) Filed: Mar. 26, 2014

(65) Prior Publication Data

US 2014/0206040 A1 Jul. 24, 2014

Related U.S. Application Data

(63) Continuation of application No. PCT/KR2012/007955, filed on Sep. 28, 2012.

(30) Foreign Application Priority Data

Sep. 30, 2011 (KR) ........................ 10-2011-0100364

(51) Int. Cl.

*C12N 1/20* (2006.01)
*C12P 19/26* (2006.01)
*C12R 1/46* (2006.01)

(52) U.S. Cl.

CPC .. *C12P 19/26* (2013.01); *C12R 1/46* (2013.01)
USPC .......................................... 435/253.4; 435/84

(58) Field of Classification Search

None
See application file for complete search history.

(56) References Cited

U.S. PATENT DOCUMENTS

| | | | |
|---|---|---|---|
| 4,784,990 | A | 11/1988 | Nimrod et al. |
| 6,090,596 | A | 7/2000 | Stahl |
| 2012/0232261 | A1 | 9/2012 | Kang et al. |

FOREIGN PATENT DOCUMENTS

| | | | |
|---|---|---|---|
| EP | 0144019 | | 6/1985 |
| JP | 362104579 A | * | 5/1987 |
| JP | 0258502 | | 2/1990 |
| JP | 10-113197 | | 5/1998 |
| KR | 10-0250573 | | 4/2000 |
| KR | 10-0472007 | | 2/2004 |
| KR | 10-2010-0048778 | | 5/2010 |
| KR | 10-2011-0029492 | | 3/2011 |
| WO | 94-00463 | | 1/1994 |

OTHER PUBLICATIONS

Widner et al., Applied and Environmental Microbiology, 2005, vol. 71, No. 7, p. 3747-3752.*
Holm et al., J. Dairy Sci., 2004, vol. 87, p. 1151-1157.*
International Search Report was mailed on Feb. 22, 2013 in International Application PCT/KR2012/007955.

* cited by examiner

*Primary Examiner* — Kade Ariani
(74) *Attorney, Agent, or Firm* — H.C. Park & Associates, PLC

(57) ABSTRACT

Provided is a *Streptococcus dysgalactiae* ID9103 strain having accession number KCTC11818BP, and a method of producing hyaluronic acid by culturing the strain to produce hyaluronic acid having an average molecular weight of 10,000,000 Da or more.

17 Claims, 3 Drawing Sheets

*STREPTOCOCCUS DYSGALACTIAE* ID9103 AND METHOD FOR PRODUCTION OF HYALURONIC ACID USING THE SAME

CROSS REFERENCE TO RELATED APPLICATIONS

This application is a continuation of International Application No. PCT/KR2012/007955, filed on Sep. 28, 2012, and claims priority from and the benefit of Korean Patent Application No. 10-2011-0100364 filed on Sep. 30, 2011, all of which are hereby incorporated by reference for all purposes as if fully set forth herein.

BACKGROUND OF THE INVENTION

1. Field

The present invention relates to a strain of genus *streptococcus* by which high molecular weight hyaluronic acid can be produced with a high yield, and a method of producing hyaluronic acid using the same. More particularly, the present invention relates to a *Streptococcus dysgalactiae* ID9103 strain having an accession number of KCTC11818BP, and a method of producing hyaluronic acid comprising culturing the strain.

2. Discussion of the Background

Hyaluronic acid ((HA), Hyaluronan, $(C_{14}H_{20}NNaO_{11})n$ (n>1000)) is a polymer existing throughout living organisms, and is a polysaccharide, called glycosaminoglycan. It has a structure which is composed of alternating D-glucuronic acid and N-acetylglucosamine, linked together via alternating β-1,3 and β-1,4 glycosidic bonds. It is a water-soluble material and its usable molecular weight has a wide range of 1,000 to 10,000,000 Da (daltons). Also, it has a structure of a straight chain.

The hyaluronic acid with salt structure shows a high efficacy and a high effect, and shows a strong lubricative effect in a physical friction state due to its high moisturizing effect. Also, it has preferable advantages in various effects and properties such as protection against bacterial invasion, etc. Thus, the development using the hyaluronic acid has been recently conducted in the field of medical treatment. These advantages can be applied to medical supplements, bio materials, and foods as well as play a role in medical supplies or cosmetics. Further, novel fields based on hyaluronic acid have been continuously developed.

In order to develop hyaluronic acid, a biological tissue extraction method or a microorganism culturing method is used. however, since a chicken comb extraction method causes many disadvantages such as virus invasion, impurities, and inflammatory reactions, a microorganism culturing production method has been recently mainly used in which a molecular weight and productivity can be controlled, and a high quality of raw materials can be obtained. Especially, in a recent tendency, according to the range of a molecular weight of hyaluronic acid adjusted and produced by microorganism culturing, use of hyaluronic acid is determined. Ultra-low molecular weight hyaluronic acid of 100,000 Da or less is mainly used for foods or cosmetics, and low molecular weight hyaluronic acid with an average molecular weight of 1,000,000 Da is utilized for developing an eye-drops raw material or its derivative, and hyaluronic acid with an average molecular weight of 3,000,000 to 4,000,000 Da is highly valuable when utilized as a knee joint injection raw material.

Of course, there is much room for hyaluronic acid with a range of higher molecular weights to be very variously utilized. It is expected that its utilization as a knee joint therapeutic agent but also as an ophthalmic surgery adjuvant can be highly increased. Moreover, since a role of ultra-high molecular weight hyaluronic acid is needed in many areas within a body, the ultra-high molecular weight hyaluronic acid may sufficiently substitute for a conventional hyaluronic acid linking material obtained by increasing the molecular weight, the viscosity or the elasticity of relatively low molecular weight hyaluronic acid.

It can be found that most of main patents applied in Korea are limited to invention of high molecular weight hyaluronic acid. Korean Registered Patent No. 10-0250573 (LG) discloses production of hyaluronic acid of 3,500,000 Da, and Korean Registered Patent 10-0472007 (Vacctech, Kolon) discloses a technology of producing hyaluronic acid with an average molecular weight of 5,500,000 Da. Most of foreign countries (U.S. Pat. No. 4,784,990, JP2058502, and EP144019) have technologies of producing hyaluronic acid of 4,000,000 Da or less. Especially, in a case of the technology of U.S. Pat. No. 6,090,596, hyaluronic acid with a high molecular weight can be produced, but it is difficult to industrially use this technology in actuality due to its very low productivity and its production method, and also its economical efficiency is not secured.

It is known that generally widely developed hyaluronic acid with a high molecular weight of 3,000,000~4,000,000 Da is very insufficient in view of efficacy/effect to be applied to in a medical field requiring high viscosity/elasticity. In order to solve such a disadvantage, it is required to invent a technology for economically efficiently producing hyaluronic acid with an ultra-high molecular weight of 6,000,000 Da or more. Further in order to properly develop ultra-high molecular weight hyaluronic acid as a highly value-added industrial drug, the technology has to be developed as a technology with competitiveness and economical efficiency through the most creative method.

Accordingly, in order to overcome the disadvantage, it is required to develop a method of producing high molecular weight hyaluronic acid with high productivity through creative and economically efficient composition of a microorganism culture medium, and application of a mass production technology.

SUMMARY OF THE INVENTION

Accordingly, the inventors of the present invention have researched a method of efficiently producing high molecular weight hyaluronic acid, and then secured *Streptococcus dysgalactiae* ID9103, that is a non-hemolytic mutant strain without hyaluronic acid lyase. By establishing its optimum culturing condition, they completed this invention.

Accordingly, an object of the present invention is to provide *Streptococcus dysgalactiae* ID9103 strain having an accession number of KCTC11818BP.

Another object of the present invention is to provide a method of producing hyaluronic acid, comprising the step of culturing the strain in a medium comprising a carbon source and a nitrogen source.

A further object of the present invention is to provide a method of adjusting a molecular weight of hyaluronic acid, comprising the step of culturing a microorganism of genus *streptococcus* in a medium comprising at least one nitrogen source selected from the group comprising neopeptone, casein peptone and casein enzymatic hydrolysate, and at least one amino acid selected from the group comprising glutamine, cysteine and lysine.

To achieve the above-mentioned object, the present invention provides *Streptococcus dysgalactiae* ID9103 strain having an accession number of KCTC11818BP.

To achieve another above-mentioned object, the present invention provides a method of producing hyaluronic acid, comprising the step of culturing the strain in a medium comprising a carbon source and a nitrogen source.

To achieve still another above-mentioned object, the present invention provides a method of adjusting a molecular weight of hyaluronic acid, comprising the step of culturing a microorganism of genus *streptococcus* in a medium comprising at least one nitrogen source selected from the group comprising neopeptone, casein peptone and casein enzymatic hydrolysate, and at least one amino acid selected from the group comprising glutamine, cysteine and lysine.

Hereafter, the present invention may be described in detail.

The present invention provides *Streptococcus dysgalactiae* ID9103 strain having an accession number of KCTC11818BP.

The inventive *Streptococcus dysgalactiae* ID9103 strain is characterized in that it is non-hemolytic, and does not express hyaluronidase. Also, the inventive *Streptococcus dysgalactiae* ID9103 strain is characterized in that it produces high molecular weight hyaluronic acid with high production efficiency.

The inventive *Streptococcus dysgalactiae* ID9103 strain is a novel microorganism, which is obtained by separating hyaluronic acid-producing strains from among microorganisms separated from cow feces, causing mutation in the strains, and selecting a non-hemolytic strain that does not produce hyaluronic acid lyase.

The above mentioned inventive *Streptococcus dysgalactiae* ID9103 strain was identified as a microorganism of genus *streptococcus* through an identification experiment in accordance with Bergey's manual, and then identified as dysgalactiae of genus *streptococcus* through identification using an Api 20 strep kit. Thus, it was named *Streptococcus dysgalactiae* ID9103, and deposited at Korean collection for Type Culture (www.kctc.re.kr), Korean Collection for Type Cultures (KCTC), Biological Resource Center (BRC), Korea Research Institute of Bioscience and Biotechnology (KRIBB), 125 Gwahak-ro, Yuseong-gu, Daejeon 305-806, Korea, on Dec. 2, 20 2010 under accession number: KCTC 11818BP.

Also, the present invention provides a method of producing hyaluronic acid, comprising the step of culturing the inventive *Streptococcus dysgalactiae* ID9103 strain in a medium comprising a carbon source and a nitrogen source.

The inventive *Streptococcus dysgalactiae* ID9103 strain may be cultured by a conventional method for culturing a microorganism of genus *streptococcus*. The culture medium may comprise the carbon source and the nitrogen source, and further comprise amino acid.

There is no specific limitation in the inventive culture method. For example, batch, fed-batch, continuous and culture methods may be used. In the present invention, a fed-batch culture method may be preferably used. In the fed-batch culturing, a medium to be supplied to a fed-batch may comprise a nitrogen source, or both a nitrogen source and a carbon source. More preferably, the nitrogen source is casein enzymatic hydrolysate, and the carbon source is glucose.

There is no limitation in the carbon source, as long as it is a known carbon source capable of being used in microorganism culturing. Preferably, it may be selected from the group comprising glucose, fructose, maltose, lactose, galactose, glycerol and a mixture thereof. More preferably, it may be glucose.

There is no limitation in the nitrogen source, as long as it is a known nitrogen source capable of being used in microorganism culturing. Preferably, it may be selected from the group comprising yeast extract, casein peptone, casein acid hydrolysate, casein enzymatic hydrolysate, bacto-peptone, casitone, neopeptone and a mixture thereof. More preferably, it may be a mixture of yeast extract and casein enzymatic hydrolysate.

The casein enzymatic hydrolysate is obtained by enzymatic decomposition of casein. For example, it may be tryptone, tryptone T, tryptone X, BBL biosate peptone, DIPCO casein digest, bacto-casitone, BBL trypticasepeptone, bactotryptone, Bitec tryptone, NZ amine A, NZ amine AS, NZ amine EKC, NZ amine L concentration, NZ case, NZ case M, NZ case ME, NZ case plus, NZ case TT, pepticase, tryptone USP, pancreatic digest casein codex, pancreatic digest casein, enzymatic hydrolyzed casein kosher, or tryptone V.

The casein acid hydrolysate may be casein acid hydrolysate, BBL acidicase peptone, bacto-casamino acid, bacto-casamino acid technical, amicase, hicase amino, hiKM, hicaseSF, or acid-decomposed casein.

Also, the inventive medium may further comprise amino acid. There is no limitation in the kind of the amino acid to be added. Preferably, it may be selected from the group comprising glutamine, lysine, cysteine, arginine, methionine, aspartic acid, glycine and a mixture thereof, and more preferably, may be lysine.

More preferably, the inventive medium composition may comprise casein enzymatic hydrolysate as the nitrogen source, and lysine as amino acid. When the inventive strain is cultured in the culture medium comprising casein enzymatic hydrolysate together with lysine, the amount of hyaluronic acid produced by the strain is increased, and hyaluronic acid having a very high average molecular weight is produced.

There is no specific limitation in the concentrations of casein enzymatic hydrolysate and lysine. Preferably, the casein enzymatic hydrolysate is comprised at a concentration of 0.5% (w/v) to 3% (w/v), and the lysine is comprised at a concentration of 0.015% (w/v) to 0.6% (w/v).

The inventive *Streptococcus dysgalactiae* ID9103 strain may be used to produce ultra-high molecular weight hyaluronic acid having an average molecular weight of 10,000,000 Da or more with a high yield of 9 g/L or more.

Meanwhile, the present invention provides a method of adjusting a molecular weight of hyaluronic acid, comprising the step of culturing a microorganism of genus *streptococcus* in a medium comprising a nitrogen source selected from the group comprising neopeptone, casein peptone and casein enzymatic hydrolysate, and amino acid selected from the group comprising glutamine, cysteine and lysine.

There is no limitation in the microorganism of genus *streptococcus*, as long as it produces hyaluronic acid and is comprised in genus *streptococcus*. Preferably, it may be the inventive *Streptococcus dysgalactiae* strain, and more preferably, may be *Streptococcus dysgalactiae* ID9103 (accession number: KCTC 11818BP) strain.

The molecular weight indicates an average molecular weight of hyaluronic acid, and the adjustment indicates that the kinds of nitrogen source and amino acid are changed so as to produce hyaluronic acid having a specific range of molecular weights. The molecular weight range of hyaluronic acid is not specifically limited. Preferably, the molecular weight may range from 6,000,000 Da to 7,000,000 Da, 7,000,000 Da to 8,000,000 Da, 8,000,000 Da to 9,000,000 Da, or 9,000,000 Da to 11,000,000 Da.

Also, according to the inventive production method, by using the inventive *Streptococcus dysgalactiae* ID9103 strain, as required, it is possible to produce ultra-high molecular weight hyaluronic acid having various average molecular weights of 6,000,000 Da or more with high yield.

Specifically, when the inventive strain is cultured in a medium comprising neopeptone and glutamine, or a medium comprising casein peptone and cysteine, it is possible to produce hyaluronic acid having an average molecular weight of 6,000,000 Da to 7,000,000 Da.

When the inventive strain is cultured in a medium comprising casein enzymatic hydrolysate and glutamine, or a medium comprising casein peptone and lysine, it is possible to produce hyaluronic acid having an average molecular weight of 7,000,000 Da to 8,000,000 Da.

When the inventive strain is cultured in a medium comprising casein enzymatic hydrolysate and lysine, it is possible to produce hyaluronic acid having an average molecular weight of 8,000,000 Da to 9,000,000 Da.

When the inventive strain is cultured in a medium comprising casein enzymatic hydrolysate and lysine through a method of supplying the casein enzymatic hydrolysate in a fed-batch manner, it is possible to produce hyaluronic acid having an average molecular weight of 9,000,000 Da to 11,000,000 Da.

The average molecular weight described in this invention indicates a weight average molecular weight.

The effects of the invention are shown through an Example of the present invention.

In an Example of the present invention, about 500 samples collected from 10 stables of the whole country were smeared on 3.7% brain heart infusion solid medium, and colonies producing a viscous substance were separated. Then, coccus with a chain structure through a microscope was selected, and a gram-positive strain was selected through a gram staining method. The selected strain was cultured and then, through a carbazole method and a turbidity analysis, a strain producing hyaluronic acid was separated. By causing mutation in the separated strain, a non-hemolytic strain that does not express hyaluronidase enzyme was separated. As a result, it was determined that the inventive *Streptococcus dysgalactiae* ID9103 strain does not express hyaluronidase enzyme, does not show hemolyticity, and is excellent in hyaluronic acid production capacity. Then, through identification, it was identified as dysgalactiae of genus *streptococcus*, and deposited with an accession number of KCTC11818BP at Korean Collection for Type Culture (KCTC) on Dec. 2, 2010.

In one Example in the present invention, a conventional *Streptococcus dysgalactiae* and the inventive strain were cultured under the same condition so as to measure the production rate and the viscosity of hyaluronic acid. As a result, it was found that the inventive strain shows higher hyaluronic acid production capacity than the conventional strain by 20% or more, and shows significantly higher viscosity than the conventional strain. Thus, it was determined that the inventive strain is a strain that can efficiently produce high molecular weight hyaluronic acid.

In another Example of the present invention, a culturing condition that can increase the hyaluronic acid production capacity of the inventive *Streptococcus dysgalactiae* ID9103 strain was established. By measuring hyaluronic acid production capacity and culture solution viscosity according to concentrations of Yeast extract, kinds and concentrations of amino acid, and kinds and concentrations of a nitrogen source, medium compositions that show high production capacity and can produce high molecular weight hyaluronic acid were selected. Through a culturing test using a combination of these conditions, an optimum culturing condition was established. Specifically, it was found that when yeast extract is comprised in the composition at a concentration of 0.75% or more, the production of hyaluronic acid is increased, and the average molecular weight of hyaluronic acid is increased. It was found that when lysine, cysteine, arginine or methionine is used, high molecular weight hyaluronic acid is produced, and also it was found that when casein acid hydrolysate, casein enzymatic hydrolysate or neopeptin is used as a nitrogen source, high molecular weight hyaluronic acid is produced.

In another Example in the present invention, it was found that when *Streptococcus dysgalactiae* ID9103 strain is cultured by the combination of various culturing condition as obtained above, various high molecular weight hyaluronic acids having a molecular weight of 6,000,000, 7,000,000 or 8,000,000 Da can be produced. Accordingly, it was found that a required various high molecular weight hyaluronic acid can be produced with high efficiency through the inventive strain and the inventive culturing method.

Also, in one Example in the present invention, when the strain was cultured in a medium composition comprising casein enzymatic hydrolysate and lysine, the amount of produced hyaluronic acid was increased, and the average molecular weight of the produced hyaluronic acid was significantly increased. Thus, proper concentrations were tested. As a result, it was found that when the casein enzymatic hydrolysate is comprised at a concentration of 0.5% (w/v) to 3% (w/v), and the lysine is comprised at a concentration of 0.015% (w/v) to 0.6% (w/v), hyaluronic acid with an average molecular weight of 8,000,000 Da or more can be produced with high efficiency.

In another Example in the present invention, it was found that when the casein enzymatic hydrolysate and a basic medium composition (glucose) are supplied in a fed-batch manner in a fed-batch culture method, ultra-high molecular weight hyaluronic acid having an average molecular weight of 10,000,000 Da or more was produced with very high efficiency of is 9.0 g/L or more.

The present invention provides a strain of genus *streptococcus* by which high molecular weight hyaluronic acid can be produced with a high yield, and a method of producing hyaluronic acid using the same. The inventive strain can produce highly value-added ultra-high molecular weight hyaluronic acid with a high yield. In the inventive method, according to compositions of a medium, it is possible to produce various ultra-high molecular weight hyaluronic acids, and produce ultra-high molecular weight hyaluronic acid having an average molecular weight 10,000,000 Da or more to the maximum.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

Figure 1:
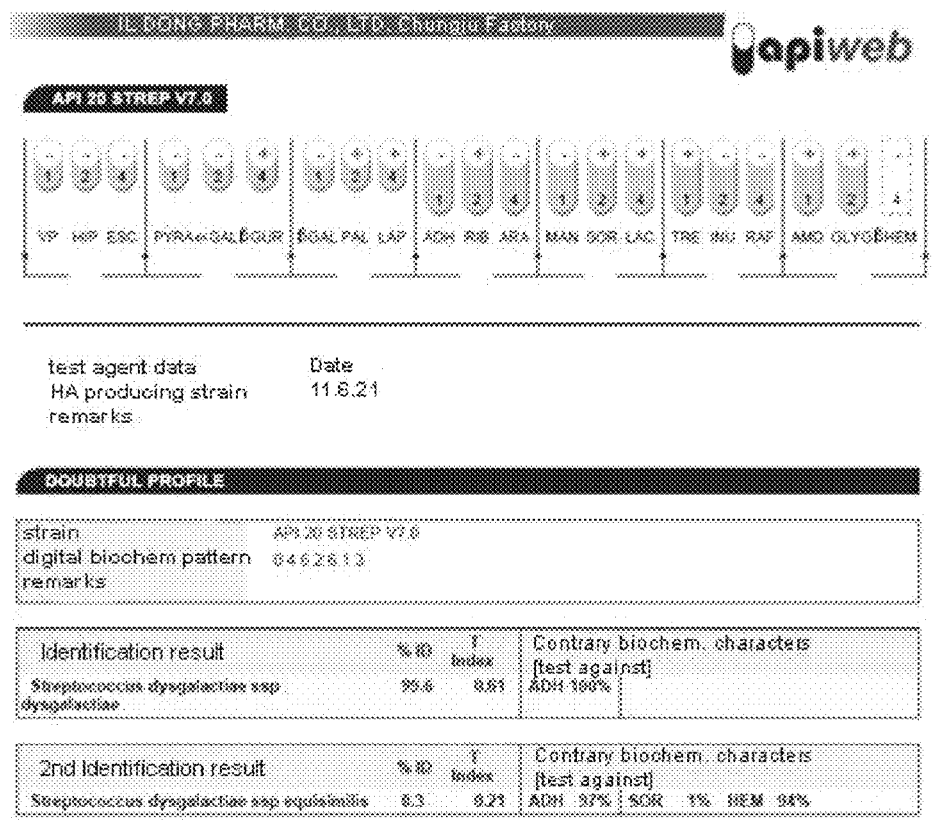
FIG. 1 shows the identification result of the inventive *Streptococcus dysgalactiae* ID9103 strain, identified by an Api kit.

Hereinafter, exemplary embodiments of the present invention will be described with reference to the accompanying drawings.

In the following description and drawings, the same reference numerals are used to designate the same or similar components, and so repetition of the description on the same or similar components will be omitted.

EXAMPLE 1

Selection of *Streptococcus dysgalactiae* ID9103

<1-1> Securing of Strain of Genus *Streptococcus* Producing Hyaluronic Acid

Genus *streptococcus* producing hyaluronic acid (HA) is well grown in a brain heart infusion medium (Calf brains, infusion 0.77%, beef hearts, infusion 0.98%, proteose peptone 1%, dextrose 0.2%, NaCl 0.5%, Disodium phosphate 0.25%; BD, US), and in single colony separation, it can produce hyaluronic acid, thereby forming more smooth and viscous colonies than general colonies.

About 500 samples collected from 10 stables of the whole country were diluted in such a manner that about 200 colonies can be grown per solid medium, and smeared on 3.7% brain heart infusion solid medium. Then, with the naked eye, colonies that were found to produce a viscous substance were selected.

In order to morphologically observe separated strains, they were smeared on a brain heart infusion solid medium so as to separate colonies, and cultured in a 37° C. culture medium. When the colonies were formed, one drop of sterilized distilled water was dropped on a slide glass. Then, one colony was placed on the tip of a sterilized toothpick and dissolved in distilled water. It was covered with a cover glass, and coccus with chain structure, like genus *streptococcus*, was selected by enlargedly observing microbial cells through a microscope (×400).

In order to select gram-positive genus *streptococcus*, a sample on a slide glass was prepared through a gram staining method in the above described method, and was slightly heated on a lamp so as to attach bacteria on the slide glass. About 1 minute later after staining with dye, the dye was washed with slightly flowing water. When the water was dried to some extent, one drop of mineral oil was dropped thereto. The sample was covered with a cover glass, and observed by a microscope. Herein, the stained gram-positive bacteria are colored violet. Through this method, suitable strain candidates were selected.

In order to determine if a viscous substance produced by each strain is HA, HA production was confirmed. In order to confirm the production of HA, a carbazole reaction and a cetyltrimethyl-ammonium bromide (CTAB) reaction are used. The carbazole reaction is a method of measuring the amount of glucuronic acid produced by decomposition of HA by sulfuric acid. After the production of HA by the carbazole reaction was confirmed, the CTAB reaction was carried out so as to confirm HA production. CTAB destroys a mucous membrane and makes it opaque. HA is a viscous substance, and thus forms an insoluble complex and becomes opaque by being destroyed by CTAB. The carbazole reaction has a disadvantage in that since glucuronic acid produced by other sugars is measured, HA in a higher amount may be measured in a culture solution state than in an actual amount. Since CTAB reacts with only HA, it is possible to simply confirm HA production within a short time. Through the carbazole reaction, strains producing polysaccharide including HA were selected, and from among the strains, through the CTAB reaction, a strain producing HA was selected.

The carbazole reaction is a method in which uronic acid can be quantitated. Glucuronic acid, one of materials constituting hyaluronic acid, is colored purple by the reaction, and thus can be quantitated. In the carbazole reaction, 1 ml of a sample was dissolved in 5 ml of 0.025M (in $H_2SO_4$) sodium tetraborate decahydrate, sufficiently mixed, and boiled in water for 10 minutes. After being cooled in ice, it was added and mixed with 200 ul of 0.1% (in EtOH) Carbazole, and boiled in water for 10 minutes. At 525 nm, the absorbency was measured.

In the CTAB reaction, 1/10-diluted culture solution was diluted again to half concentration with 0.03% SDS solution. Then, 200 ul of the resultant solution was mixed with 200 ul of acetic acid buffer (sodium acetate 1.55%, acetic acid 0.063%, NaCl 0.88%), and reacted at 37° C. for 30 minutes. 800 ul of CTAB solution was added thereto. At 600 nm, the absorbency was measured.

<1-2> Securing of Non-Hemolytic Mutant Strain with No Hyaluronidase Activity

The hyaluronic acid-producing strain selected in Example <1-1> was shake-cultured in 50 ml of 3.7% brain heart infusion liquid medium for 24 hours at 37° C. A culture solution with OD (600) of 0.3 was treated with N-Methyl-N'-nitro-N-nitrosoguanidine (NTG), followed by stirring at 37° C. for 1 hour so as to determine the condition at a lethal rate of 95%. The culture solution treated with 10 mg/ml of NTG was centrifuged at a rotation speed of 4000 rpm for 10 minutes, and the microbial cells were collected and washed with 50 mM Tris-maleate buffer (pH 8.0) three times. The spores on which mutation was induced were diluted with sterilized saline solution at a concentration of $10^2$~$10^4$/ml, and were smeared on a brain heart infusion solid medium including 5% sheep blood and cultured at 37° C. Then, non-hemolytic colonies without a clear zone made by destruction of erythrocytes were selected. However, because hemolyticity may occur again, NTG mutation for such non-hemolytic colonies was repeatedly performed. Then, colonies that do not show hemolyticity in subculture were selected.

From among the secured non-hemolytic strains, colonies that do not express hyaluronidase enzyme were selected by CTAB reaction described in Example 1-1. The secured non-hemolytic strains were cultured for one day in a brain heart infusion solid medium added with 0.1% hyaluronic acid, and 10% CTAB was added to the upper layer. From among colonies with no hyaluronidase activity, *Streptococcus dysgalactiae* ID9103 having no clear zone around itself was selected.

<1-3> Identification of Selected Strain

In order to identify the strain as genus *streptococcus* based on biochemical characteristics in Bergey's manual, in an identification experiment, a basic medium including yeast extract and peptone was added with sugar or amino acid required for determining biochemical characteristics, and the color change was changed. The sources added to the medium comprise inulin, lactose, mannitol, raffinose, ribose, salicin, sorbitol, trehalose, arginine, esculin, and hippurate. Herein, bromperesol purple (BCP) was added thereto, and the color change between the strain and a non-inoculated control was observed. BCP is colored violet at neutral pH, yellow at acidic pH, and red at basic pH. Before being inoculated with microbial cells, the medium is neutral, and colored violet.

As a result, the inventive *Streptococcus dysgalactiae* ID9103 strain showed a highly similar characteristic to dysgalactiae of genus *streptococcus* based on Bergey's manual. This result is noted in Table 1.

TABLE 1

| | Biochemical characteristics | | | | | | | | |
|---|---|---|---|---|---|---|---|---|---|
| | Inulin | Lactose | Mannitol | Raffinose | Ribose | Trehalose | Arginine | Esculin | Hippurate |
| Control group | − | + | − | − | + | + | − | − | − |
| Test group | − | + | − | − | + | + | + | − | − |

The *Streptococcus dysgalactiae* ID9103 strain selected in Example <1-2> was identified using an Api kit. By using an Api 20 strep kit (Biomerieux, France) for identification of *streptococcus*, the identification was performed following the manufacturer's manual. On a solid medium, the strain was sufficiently dissolved in 2 ml of suspension medium by using a cotton swab so as to prepare inoculation liquid with 4 McFarland turbidity. The strep comprises a total of 20 cupules including VP, HIP, ESC, PYRA, αGAL, βGUR, βGAL, PAL, LAP, ADH, RIB, ARA, MAN, SOR, LAC, TRE, RAF, AMD, and GLYG in order, and they cause different reactions, respectively. To VP to LAP each, the inoculation liquid was filled in an amount of 100 ul, and to others, the inoculation liquid in an amount of 500 ul mixed with 2 ml of GP medium was filled in an amount of 100 ul. ADH and GLYG were added with mineral oil. After culturing for 4 hours, VP was added with one drop of VP1 and VP2 each, HIP was added with two drops of NIN reagent, and PYRA to LAP were added with one drop of ZYM A, and ZYM B reagents each. After 10 minutes, the results were measured, and after 24 hours, the results on other cupules were read again.

As a result, as shown in FIG. 1, it was identified the inventive *Streptococcus dysgalactiae* ID9103 is dysgalactiae of genus *streptococcus*.

The *Streptococcus dysgalactiae* ID9103 was deposited with an accession number is of KCTC11818BP at Korean Collection for Type Culture (KCTC) on Dec. 2, 2010.

EXAMPLE 2

Basic Culturing Condition Test on Production of High Molecular Weight Hyaluronic Acid, and Production Amount Comparison Test <2-1> Basic Culturing Condition Test 4 ml of *Streptococcus dysgalactiae* ID9103 strain culture solution stored in a −72° C. refrigerator was rapidly thawed, smeared on 5.2% brain heart infusion solid medium, and cultured at 37° C. for 24 hours. The grown colony was cut with an area of 1 $cm^2$ and inoculated into 40 ml of 3% Todd-Hewitt broth sterilized liquid medium (heart, infusion 0.31%, neopeptone 2%, dextropse 0.2%, NaCl 0.2%, Disodium phosphate 0.04%, sodium carbonate 0.25%; BD, US).

40 ml of the liquid shake-cultured at 37° C. at 120 rpm was used as a primary seed culture solution. In a Logarithmic growth phase following culturing for 6 hours, the primary seed liquid was aseptically inoculated to three 3% Todd-Hewitt broth sterilized liquid media (40 ml, pH 7.8). Under the culturing condition of 37° C. and 120 rpm, after aseptic culturing for 20 hours or more, the cultured medium was used as a secondary seed culture solution. Herein, the secondary seed culture solution has to be maintained at pH of 6.4±0.2, and have OD (600) of 0.35±0.05. 120 ml of the secondary seed culture solution was inoculated to a main culture medium, followed by culturing for 40 hours or more. According to a rotation speed of a fermentation bath impeller, a culturing temperature, and a medium composition, the difference between hyaluronic acids in the productivity was observed. Then, the condition for increasing the hyaluronic acid productivity was determined. This culturing process was performed in the same manner in all Examples.

The main culture medium determining test for optimally producing hyaluronic acid was performed in a 5 L fermentation bath under 3.5 L culture solution condition. The medium composition comprised glucose 6% (w/v), yeast extract 0.5% (w/v), casein peptone 2% (w/v), glutamine 0.06% (w/v), sodium gluconate 0.1% (w/v), oxalic acid 0.02% (w/v), magnesium sulfate 0.15% (w/v), potassium phosphate dibasic 0.25% (w/v), sodium chloride 0.5% (w/v), sodium acetate 0.5% (w/v), ferric chloride 0.007% (w/v), and ammonium molybdate 0.05% (w/v). The test was basically performed under the condition of pH 7.0, and 34° C.

In the present invention, the hyaluronic acid concentration in the culture solution was confirmed by both a carbazole method (T. Bitter, Anal. Biochem., 1962, 4, 330-334) and a turbidity analysis (S. Jung-Min, Carbohyd. Polym., 2009, 78, 633-634).

The viscosity analysis was performed by using LVDV-1 (Brookfield, US), in which the viscosity (cP) was measured by analyzing the test sample under the condition of spindle No S31, RPM 3.0 and the sample temperature of 25° C.

The amount of microbial cells was measured by transferring 200 ul of the culture solution diluted to an appropriate concentration (1/10 of culture solution) to a 96 well microplate, and measuring the absorbency at wavelength of 600 nm by Multi-detection Microplate reader (BioTek, US).

The rotation speed of the fermentation bath impeller is important because the impeller performs a role of helping growth of microbial cells by allowing oxygen and nutrients to be uniformly mixed with medium. When the rotation speed was set to be 100 to 500 rpm, the culturing result of ID9103 is noted in table 2.

At each impeller rotation speed, the amount of produced hyaluronic acid, and the amount of microbial cells were similar to each other while the viscosity was increased. Thus, it was found that a low impeller rotation speed is helpful in increasing the molecular weight. Accordingly, in the tests of the following Examples, the impeller rotation speed of the fermentation bath was fixed as 100 rpm.

TABLE 2

Concentration of hyaluronic acid according to impeller rotation speed

| impeller rotation speed (rpm) | Conc. of hyaluronic acid (g/L) | amount of microbial cells (A600) | viscosity (cP) |
|---|---|---|---|
| 100 | 7.468 | 2.540 | 2860 |
| 300 | 7.452 | 2.765 | 1210 |
| 500 | 7.431 | 2.687 | 870 |

<2-2> Comparison Test on Amount of Produced Hyaluronic Acid

A conventional *Streptococcus dysgalactiae* strain, and the inventive *Streptococcus dysgalactiae* ID9103 strain were cultured under the same condition, and the amounts of produced hyaluronic acid were compared.

The medium composition and the culturing condition were the same as described in Example <2-1>, and the impeller speed was set as 100 rpm.

As a result, as noted in table 3, it found that the inventive strain shows a higher production amount of hyaluronic acid than the conventional strain by 20% or more under the same condition. Especially, it was found that the inventive strain shows significantly higher viscosity than the conventional strain. Thus, it was determined that the inventive strain is a strain efficiently producing high molecular weight hyaluronic acid.

TABLE 3

Concentration of hyaluronic acid compared a conventional *Streptococcus*

| Strain | Conc. of hyaluronic acid (g/L) | amount of microbial cells (A600) | viscosity (cP) |
|---|---|---|---|
| ID9102 | 6.039 | 3.710 | 1680 |
| ID9103 | 7.311 | 2.881 | 2580 |

EXAMPLE 3

High Molecular Weight Hyaluronic Acid Productivity According to Adjustment of Yeast Extract Concentration Based on the culturing condition and the medium composition determined in <Example 2>, the culturing was performed by varying the concentration of yeast extract. The nitrogen source is known to perform an important role in metabolism of microorganisms, and have an effect on production of hyaluronic acid. Accordingly, it was determined that the adjustment of the concentration of the yeast extract as the nitrogen source may contribute to the productivity of hyaluronic acid.

As a result, as noted in table 4, the viscosity was increased at 2% (w/v) of yeast extract, as compared to that at 0.5% (w/v) of yeast extract. Accordingly, it was determined that the increase of yeast extract concentration is suitable for producing high molecular weight hyaluronic acid. In the tests of following Examples, the concentration of the yeast extract was increased up to 2% (w/v).

TABLE 4

Concentration of hyaluronic acid according to concentration of yeast extract

| Con. of yeast extract (%(w/v)) | Conc. of hyaluronic acid (g/L) | amount of microbial cells (A600) | viscosity (cP) |
|---|---|---|---|
| 0.5 | 7.490 | 2.365 | 2620 |
| 2 | 7.896 | 2.565 | 3370 |
| 3.5 | 7.782 | 2.820 | 3050 |

EXAMPLE 4

Effect of Amino Acid on Hyaluronic Acid Production

Based on the culturing condition and the medium composition determined in previous Examples, it was confirmed how various amino acids have an effect on the production of high molecular weight hyaluronic acid. The amino acids used in this Example are noted in table 5. Conventional glutamine was replaced by amino acids in table 5.

As a result, as noted in table 5, groups using lysine, cysteine or arginine produced hyaluronic acid in an amount of 8 g/L or more, and other groups comprising lysine, cysteine, arginine or methionine showed higher viscosity than a control group. Especially, a group comprising lysine showed a much higher viscosity (4,230 cP) than the control group.

TABLE 5

Hyaluronic acid production according to amino acids

| amino acid | Conc. of hyaluronic acid (g/L) | amount of microbial cells (A600) | viscosity (cP) |
|---|---|---|---|
| glutamin | 7.501 | 2.472 | 3170 |
| lysine | 8.111 | 2.511 | 4230 |
| cysteine | 8.034 | 2.503 | 4160 |
| arginine | 8.211 | 2.626 | 3890 |
| methionine | 7.992 | 2.803 | 3940 |
| aspartic acid | 7.861 | 2.721 | 2790 |
| glycine | 7.792 | 2.398 | 2980 |

EXAMPLE 5

Effect of Amino Acid Concentration on Hyaluronic Acid Production

In order to determine a proper medium concentration on lysine, cysteine, arginine, and methionine showing high viscosity in <Example 4>, each amino acid was added at various concentrations, followed by culturing. Then, the concentration of hyaluronic acid, the amount of microbial cells, the viscosity of culture solution and the like were measured.

Figure 2:
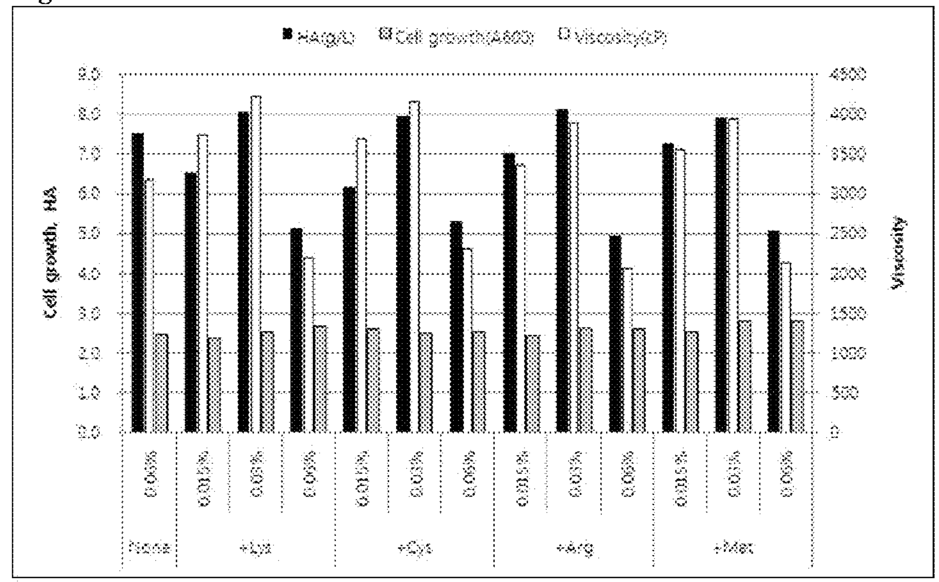
FIG. 2 is a graph showing the amount of produced hyaluronic acid, the viscosity of a culture solution, and the amount of microbial cells, according to kinds and concentrations added amino acid.

As a result, as noted in table 6 and as shown in FIG. 2, 4 kinds of amino acids at a concentration of 0.03% (w/v) showed higher viscosity than at other concentrations. Lysine and cysteine showed higher viscosity levels (4230 cP and 4160 cP, respectively) than at other concentrations. Arginine and methionine showed higher viscosity levels (3890, and 3940 cP respectively) than conventional conditions although the levels did not reach 4000 cP. Under this concentration condition, hyaluronic acid was produced in an amount of about 8 g/L, which was higher than at other concentrations.

In the tests of following Examples, the amino acid concentration was fixed at 0.03% (w/v).

TABLE 6

Hyaluronic acid production according to concentration of amino acid

| amino acid/Conc. | | Conc. of hyaluronic acid (g/L) | amount of microbial cells (A600) | viscosity (cP) |
|---|---|---|---|---|
| glutamine | 0.06% | 7.542 | 2.472 | 3170 |
| lysine | 0.015% | 6.521 | 2.345 | 3740 |
| | 0.03% | 8.070 | 2.511 | 4230 |
| | 0.06% | 5.140 | 2.667 | 2200 |
| cysteine | 0.015% | 6.153 | 2.578 | 3690 |
| | 0.03% | 7.956 | 2.503 | 4160 |
| | 0.06% | 5.315 | 2.541 | 2310 |
| arginine | 0.015% | 7.032 | 2.410 | 3360 |
| | 0.03% | 8.120 | 2.626 | 3890 |
| | 0.06% | 4.952 | 2.578 | 2060 |
| methionine | 0.015% | 7.254 | 2.521 | 3560 |
| | 0.03% | 7.934 | 2.803 | 3940 |
| | 0.06% | 5.060 | 2.784 | 2120 |

EXAMPLE 6

Effect of Peptones (as a Medium Source) on Hyaluronic Acid Production

Based on the culturing condition and the medium composition determined in <Example 3>, it was determined if high molecular weight hyaluronic acid can be produced by replacing conventional casein peptone used as the nitrogen source with other peptones as a medium source. The peptones used in this Example are noted in table 7, and the concentration was 1% (w/v).

As a result, as noted in table 7, casein acid hydrolysate, casein enzymatic hydrolysate, and neopeptone showed higher viscosity levels than casein peptone. Especially, casein enzymatic hydrolysate showed a viscosity level of 4590 cp, and is positively expected to produce high molecular weight hyaluronic acid.

TABLE 7

Hyaluronic acid production according to peptones as a medium source

| peptones as a medium source | Conc. of hyaluronic acid (g/L) | amount of microbial cells (A600) | viscosity (cP) |
|---|---|---|---|
| casein peptone | 7.506 | 2.520 | 3350 |
| casein acidic hydrolysate | 7.481 | 2.774 | 3610 |
| casein enzymatic hydrolysate | 8.210 | 2.564 | 4590 |
| bacto peptone | 7.614 | 2.865 | 3050 |
| casitone | 7.210 | 3.048 | 3140 |
| neopeptone | 7.513 | 2.716 | 3420 |

EXAMPLE 7

Effect of Concentration of Peptones (as a Medium Source) on Hyaluronic Acid Production In order to determine a proper medium concentration of casein acid hydrolysate, casein enzymatic hydrolysate, and neopeptone showing high viscosity in <Example 6>, each nitrogen source was added at various concentrations, followed by culturing. Then, the concentration of hyaluronic acid, the amount of microbial cells, the viscosity of culture solution and the like were measured.

Figure 3:
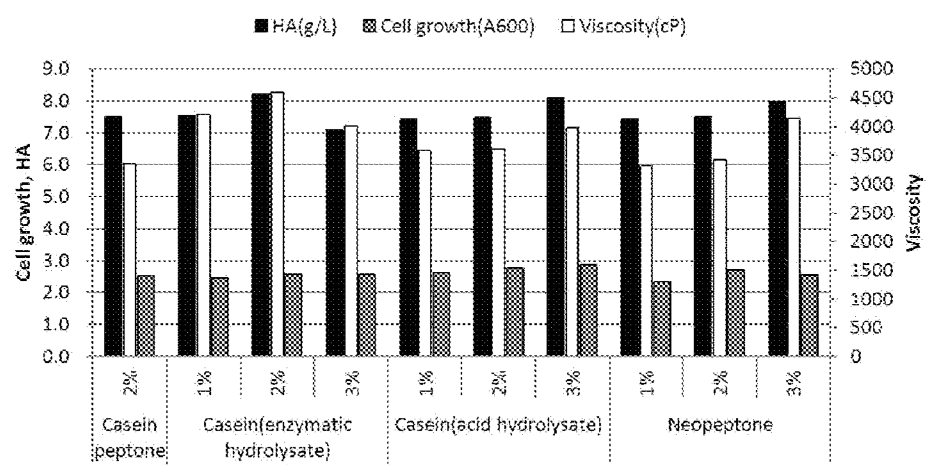
FIG. 3 is a graph showing the amount of produced hyaluronic acid, the viscosity of a culture solution, and the amount of microbial cells, according to kinds and concentrations added peptones.

As a result, as noted in table 8 and as shown in FIG. 3, casein enzymatic hydrolysate showed the highest viscosity at 1% (w/v), and casein acid hydrolysate and neopeptone showed the highest viscosity at 1.5% (w/v). Casein enzymatic hydrolysate and neopeptone showed high production amounts of 8.2 g/L, and 8.0 g/L respectively, and high viscosity levels of 4590 cP, and 4140 cP respectively. Casein acid hydrolysate showed a high production amount of 8.1 g/L but showed only a viscosity level of 3980 cP (less than 4000 cP). In the tests of following Examples, based on this result, the concentration of casein enzymatic hydrolysate was fixedly set as 1% (w/v), and the concentration of casein acid hydrolysate and neopeptone was fixedly set as 1.5% (w/v).

TABLE 8

Hyaluronic acid production according to peptones as a medium source

| peptones as a medium source/ concentration | | Conc. of hyaluronic acid (g/L) | amount of microbial cells (A600) | viscosity (cP) |
|---|---|---|---|---|
| casein peptone | 2% | 7.506 | 2.520 | 3350 |
| casein enzymatic | 1% | 7.523 | 2.463 | 4210 |
| hydrolysate | 2% | 8.210 | 2.564 | 4590 |
| | 3% | 7.103 | 2.573 | 4010 |
| casein acidic | 1% | 7.435 | 2.626 | 3580 |
| hydrolysate | 2% | 7.481 | 2.774 | 3610 |
| | 3% | 8.102 | 2.874 | 3980 |
| neopeptone | 1% | 7.438 | 2.346 | 3310 |
| | 2% | 7.513 | 2.716 | 3420 |
| | 3% | 7.982 | 2.557 | 4140 |

EXAMPLE 8

Comparison of Hyaluronic Acid Productivity According to Combination of Peptones with Amino Acid By using the combination of amino acid determined in <Example 4> and <Example 5>, with peptones determined in <Example 6> and <Example 7>, the effect on hyaluronic acid production was determined. In the medium composition comprising the combination peptones with amino acid as noted in table 9, the inventive *Streptococcus dysgalactiae* ID9103 was cultured to produce hyaluronic acid.

As a result, each combination of peptone medium sources with amino acid showed a hyaluronic acid concentration of about 8 g/L. Meanwhile, in viscosity, the combination with casein enzymatic hydrolysate showed a higher level. Especially, the casein enzymatic hydrolysate-lysine combination showed a high hyaluronic acid concentration of 8.3 g/L, and a higher viscosity level (5320 cP) than casein enzymatic hydrolysate in <Example 7> (4590 cP) by 730 cP. Thus, it was determined that high molecular weight hyaluronic acid can be produced.

TABLE 9

| Hyaluronic acid production according to combination of peptones as a medium source and amino acid | | | | |
|---|---|---|---|---|
| combination of peptones as a medium source and amino acid | | Conc. of hyaluronic acid (g/L) | amount of microbial cells (A600) | viscosity (cP) |
| casein enzymatic hydrolysate | lysine | 8.314 | 2.611 | 5320 |
| | cysteine | 8.137 | 2.526 | 4450 |
| | arginine | 8.025 | 2.801 | 4340 |
| | methionine | 7.845 | 2.724 | 4110 |
| neopeptone | lysine | 7.878 | 2.626 | 3990 |
| | cysteine | 7.945 | 2.771 | 3560 |
| | arginine | 8.043 | 2.812 | 3140 |
| | methionine | 8.224 | 2.726 | 3370 |

EXAMPLE 9

Effect of Fed-Batch of Peptones as a Medium Source on Hyaluronic Acid Production Under the condition of casein enzymatic hydrolysate-lysine combination, obtained from the results of previous Examples, the effect of casein enzymatic hydrolysate supplied in a fed-batch manner on hyaluronic acid production was determined. The treatment time and the added concentration for a final concentration 2% were noted in table 9. The concentration of finally added casein enzymatic hydrolysate was fixedly set as 2%. Herein, the non-treated group was added with 2% of the source at the initial state. The group with a treatment time of 8 hours and a treatment concentration of 0.5%, was added with 1.5% of casein enzymatic hydrolysate at the initial culturing stage, and further added with 0.5% after 8 hours.

As a result, as noted in table 10, when 1.0% was added after 24 hours, the production amount was about 7 g/L. Herein, the viscosity level (6620 cP) was higher than the non-treated group by 1500 cP. Thus, it was found that high molecular weight hyaluronic acid can be produced. However, it was found that the addition after 8 hours and 36 hours did not is significantly increase the viscosity level, and did not have a significantly higher effect as compared to the conventional condition.

TABLE 10

| Hyaluronic acid production according to fed-batch on hyaluronic acid production | | | | |
|---|---|---|---|---|
| Treating times (hour) | Treating Conc. (%) | Conc. of hyaluronic acid (g/L) | amount of microbial cells (A600) | viscosity (cP) |
| negative control | | 7.465 | 2.365 | 5120 |
| 8 hrs | 0.5% | 7.312 | 2.565 | 5580 |
| | 1% | 7.218 | 2.660 | 5810 |
| | 1.5% | 7.881 | 2.149 | 5860 |
| 24 hrs | 0.5% | 7.198 | 2.820 | 6210 |
| | 1% | 7.046 | 2.631 | 6620 |
| | 1.5% | 7.249 | 2.648 | 6590 |
| 36 hrs | 0.5% | 8.046 | 3.040 | 5610 |
| | 1% | 8.510 | 3.565 | 5180 |
| | 1.5% | 7.915 | 2.951 | 5330 |

EXAMPLE 10

Effect of Fed-Batch of Glucose on Hyaluronic Acid Production

Under the condition of casein enzymatic hydrolysate-lysine combination, obtained from the results of previous Examples, the effect of glucose supplied in a fed-batch manner on hyaluronic acid production was determined. The treatment time and the added concentration for a final concentration 6% were noted in table 11.

When 1% was added after 24 hours, the production amount was 9 g/L or more. In proportion to this, the viscosity level was 6800 cP. Thus, it was found that the production of high molecular weight hyaluronic acid can be increased.

TABLE 11

| Treating times (hour) | Treating Conc. (%) | Conc. of hyaluronic acid (g/L) | amount of microbial cells (A600) | viscosity (cP) |
|---|---|---|---|---|
| negative control | | 7.184 | 2.411 | 5150 |
| 24 hrs | 1% | 9.103 | 2.103 | 6800 |
| | 3% | 7.921 | 2.561 | 6100 |
| | 5% | 7.712 | 2.815 | 6020 |

EXAMPLE 11

Effect of Fed-Batch of Peptones Medium Source and Glucose on Hyaluronic Acid Production By using the results from Example 9 and Example 10, casein enzymatic hydrolysate was supplied at 1%, on a 24 hour cycle in a fed-batch manner to a 2% final concentration, and glucose was supplied at 1% on a 24 hour cycle in a fed-batch manner to a 6% final concentration. Then the effect on hyaluronic acid production was determined.

As a result, it was found that hyaluronic acid was produced in an amount of 9.103 g/L, and the viscosity level was 7200 cP. Through fed-batch supply of peptones as a medium source and glucose, it was found that high molecular weight hyaluronic acid can be produced and the production amount can be increased.

EXAMPLE 12

Analysis Result of Hyaluronic Acid Productivity and Average Molecular Weight in is Each Culture at 75 L Since the results in previous Examples showed a high viscosity level, through culturing in 75 L fermentation bath under the condition suitable for producing high molecular weight hyaluronic acid, the productivity was confirmed. Then, the molecular weight was analyzed by HPLC. The culturing condition and the medium composition were the same as those in previous Examples.

The average molecular weight of hyaluronic acid was obtained by agel filtration chromatography method (Narlin B. Beaty et al, Anal. Biochem., 1985, 147, 387-395). In the analysis, the column was Toyo Soda TSK gel G6000PWXL, the moving phase comprised 150 mM NaCl, 3 mM $Na_2HPO_4$ (pH7.0), and 0.02% $NaN_2$. The detection was performed by a refractive index detector (Shodex; Showa Denko K.K. Japan), and the standard substance was prepared by polyethylene oxide at 2 mg/ml concentration per molecular weight.

As a result, as noted in table 12, the hyaluronic acid produced by culturing in the combination of casein enzymatic hydrolysate-lysine showed an average molecular weight of 8,000,000 Da or more. Especially, in the culturing under the condition of casein enzymatic hydrolysate fed-batch supplied (24 hour cycle, 1%) and lysine and glucose fed-batch supplied (24 hour cycle, 1%), the molecular weight was about 10,000,000, which was higher than a basic medium culture (about 5,900,000 Da) by about 4,000,000 Da. Thus, it was found that in the inventive production method, it is possible to produce very high molecular weight hyaluronic acid. The productivity was about 9 g/L.

It was found that through the inventive production method, it is possible to produce hyaluronic acid having various average molecular weights of 6,000,000, 6,500,000, 7,000,000, 7,500,000, 8,000,000, 9,000,000, and 10,000,000 Da, with high productivity.

Specifically, when in a basic medium, casein peptone was replaced by neopeptone, or amino acid was replaced by cysteine, hyaluronic acid having an average molecular weight of 6,000,000 Da to 7,000,000 Da was produced. When in a basic medium, casein peptone was replaced by casein enzymatic hydrolysate, or amino acid was replaced by lysine, hyaluronic acid having an average molecular weight of 7,000,000 Da to 8,000,000 Da was produced. When in a basic medium, casein peptone was replaced by casein enzymatic hydrolysate, and amino acid was replaced by lysine, hyaluronic acid having an average molecular weight of 8,000,000 Da to 9,000,000 Da was produced. When in a basic medium, casein peptone was replaced by casein enzymatic hydrolysate, amino acid was replaced by lysine, and casein peptone was added in fed-batch manner, hyaluronic acid having an average molecular weight of 9,000,000 Da to 11,000,000 Da was produced.

The basic medium, as described in Example 2, indicates a medium comprising glucose, yeast extract, casein peptone, glutamine, sodium gluconate, oxalic acid, magnesium sulfate, potassium phosphate dibasic, sodium chloride, sodium acetate, ferric chloride, and ammonium molybdate.

TABLE 12

Analysis result of hyaluronic acid productivity and average molecular weight in each culture

| culture condition | Conc. of hyaluronic acid (g/L) | Retention time (min) | average MW (Da) |
|---|---|---|---|
| conventional strain in basic medium (ID9102, Example 2) | 6.851 | 7.200 | 5,197,111 |
| inventive strain in basic medium (ID9103, Example 2) | 7.896 | 7.124 | 5,888,482 |
| substitution of glutamine into lysine of basic medium | 8.103 | 6.999 | 7,011,421 |
| substitution of glutamine into cysteine of basic medium | 8.002 | 7.111 | 6,001,441 |
| substitution of glutamine into arginine of basic medium | 8.113 | 7.113 | 5,983,441 |
| substitution of casein peptone into casein enzymatic hydrolysate of basic medium | 8.023 | 6.942 | 7,526,023 |
| substitution of casein peptone into neopeptone of basic medium | 7.994 | 7.052 | 6,529,651 |
| substitution of casein peptone into casein enzymatic hydrolysate and glutamine into lysine of basic medium | 8.056 | 6.881 | 8,070,838 |
| substitution of casein peptone into casein enzymatic hydrolysate and glutamine into lysine of basic medium, casein enzymatic hydrolysate was added 1% fed-batch for 24 hrs. | 7.526 | 6.753 | 9,220,354 |
| substitution of casein peptone into casein enzymatic hydrolysate and glutamine into lysine of basic medium, glucose was added 1% fed-batch for 24 hrs. | 9.203 | 6.850 | 8,346,841 |
| substitution of casein peptone into casein enzymatic hydrolysate and glutamine into lysine of basic medium, casein enzymatic hydrolysate and glucose were added 1% fed-batch for 24 hrs. | 9.154 | 6.651 | 10,141,891 |

EXAMPLE 13

1 t Culturing Process of *Streptococcus dysgalactiae* ID9103 for Producing Hyaluronic Acid Based on the information obtained in previous Examples, in 1 t fermentation bath, hyaluronic acid was produced. Specific conditions are as follows.

A *Streptococcus dysgalactiae* ID9103 strain culture solution stored in a −20° C. refrigerator was cultured in 800 ml of 3% Todd-Hewitt broth sterilized liquid medium (pH7.8) at 37° C. for 6 hours, and then cultured in 20 L of 3% Todd-Hewitt broth sterilized liquid medium at 37° C. for 20 hours. The cultured seed culture solution was maintained at pH of 6.0, and OD of the culture solution measured at 600 nm was 0.35. This was inoculated into 500 L of sterilized liquid medium having 6% (w/v) glucose, 2% (w/v) yeast extract, 2% (w/v) casein enzymatic hydrolysate, 0.1% (w/v) lysine, 0.1% (w/v) sodium gluconate, 0.02% (w/v) oxalic acid, 0.15% (w/v) magnesium sulfate, 0.25% (w/v) potassium phosphate dibasic, 0.5% (w/v) sodium chloride, 0.5% (w/v) sodium acetate, 0.007% (w/v) ferric chloride, and 0.05% (w/v) ammonium molybdate dissolved therein, followed by culturing in a fermentation bath under the culturing condition of 34° C., 300 rpm, 0.5 vvm, and pH 7.

Figure 4:
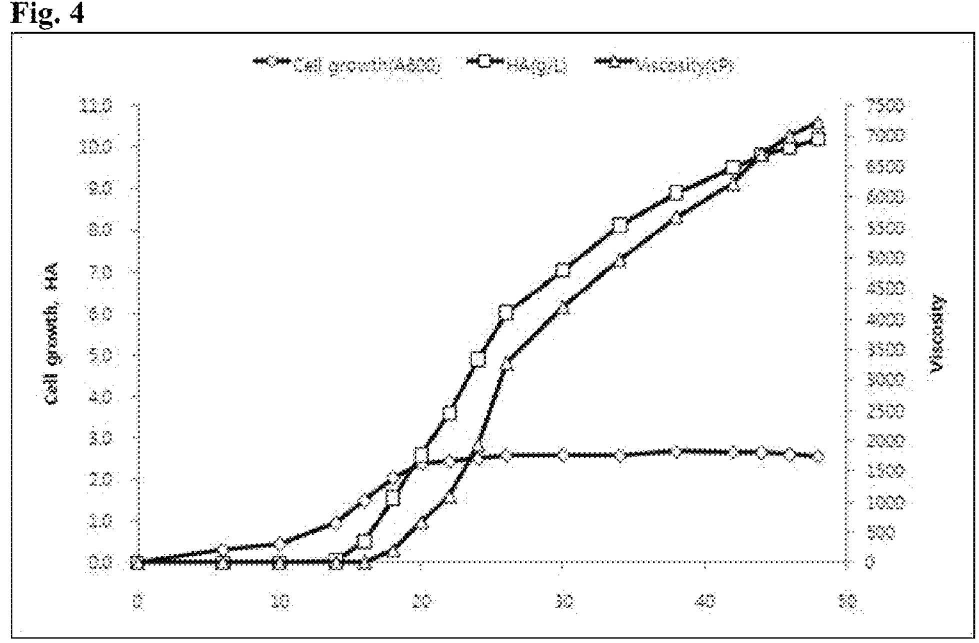
FIG. 4 is a graph showing the amount of produced hyaluronic acid, the viscosity of a culture solution, and the amount of microbial cells with lapse of production time when the inventive *Streptococcus dysgalactiae* ID9103 strain was cultured in 1 t fermentation bath in a culture medium comprising casein enzymatic hydrolysate and lysine.

When the culturing was performed in a 1 t fermentation bath for 48 hours, as shown in FIG. 4, the highest productivity (10.2 g/L) of hyaluronic acid was obtained.

After the culturing, the average molecular weight of hyaluronic acid was measured. As a result, due to the optimum culturing condition in the 1 t fermentation bath, the average molecular weight was about 10,500,000 Da, which was higher than 10,100,000 Da in 75 L fermentation bath by about 400,000 Da.

What is claimed is:

1. An isolated mutant *Streptococcus dysgalactiae* ID9103 strain deposited under the accession number KCTC 11818BP, wherein said mutant strain is chemically induced by treatment with N-methyl-N'-nitro-N-nitrosoguanidine (NTG), and wherein said mutant strain as the result of induced mutation does not produce hyaluronic acid lyase and lacks hemolytic activity.

2. A method of producing hyaluronic acid, comprising culturing the strain of claim 1 in a medium comprising a carbon source and a nitrogen source under conditions suitable to produce hyaluronic acid.

3. The method of claim 2, wherein the carbon source is selected from the group consisting of glucose, fructose, maltose, lactose, galactose, glycerol, and mixtures thereof.

4. The method of claim 2, wherein the nitrogen source is selected from the group consisting of yeast extract, casein peptone, casein acid hydrolysate, casein enzymatic hydrolysate, bacto-peptone, casitone, neopeptone, and mixtures thereof.

5. The method of claim 2, wherein the medium further comprises an amino acid.

6. The method of claim 5, wherein the amino acid is selected from the group consisting of glutamine, lysine, cysteine, arginine, methionine, aspartic acid, glycine, and mixtures thereof.

7. The method of claim 5, wherein:
the nitrogen source is casein enzymatic hydrolysate; and
the amino acid is lysine.

8. The method of claim 7, wherein:
a concentration of the casein enzymatic hydrolysate is in a range of 0.5% (w/v) to 3.0% (w/v); and
a concentration of the lysine is in a range of 0.015%(w/v) to 0.6% (w/v).

9. The method of claim 7, wherein the carbon source is glucose.

10. The method of claim 2, wherein the carbon source and the nitrogen source are supplied in a Fed-batch manner.

11. The method of claim 10, wherein:
the carbon source is glucose; and
the nitrogen source is casein enzymatic hydrolysate.

12. A method of producing hyaluronic acid having an average molecular weight of 6,000,000 Da to 7,000,000 Da comprising culturing the strain of claim 1 in a medium comprising neopeptone and glutamine.

13. A method of producing hyaluronic acid having an average molecular weight of 7,000,000 Da to 8,000,000 Da comprising culturing the strain of claim 1 in a medium comprising casein enzymatic hydrolysate and glutamine, or in a medium comprising casein peptone and lysine.

14. A method of producing hyaluronic acid having an average molecular weight of 8,000,000 Da to 9,000,000 Da comprising culturing the strain of claim 1 in a medium comprising casein enzymatic hydrolysate and lysine.

15. A method of producing hyaluronic acid having an average molecular weight of 9,000,000 Da to 11,000,000 Da comprising culturing the strain of claim 1 in a medium comprising lysine and casein enzymatic hydrolysate,
wherein the casein enzymatic hydrolysate is supplied in a Fed-batch manner.

16. A method of producing hyaluronic acid having an average molecular weight of 6,000,000 Da to 7,000,000 Da comprising culturing the strain of claim 1 in a medium comprising casein peptone and cysteine.

17. A method of producing hyaluronic acid having an average molecular weight of 6,000,000 Da to 7,000,000 Da comprising culturing the strain of claim 1 in a medium comprising neopeptone and glutamine, or in a medium comprising casein peptone and cysteine.

* * * * *